United States Patent [19]

Dakin

[11] Patent Number: 4,941,747

[45] Date of Patent: Jul. 17, 1990

[54] OPTICAL SENSING ARRANGEMENTS

[75] Inventor: John P. Dakin, Hampshire, England

[73] Assignee: Plessey Overseas Limited, Ilford, England

[21] Appl. No.: 308,521

[22] Filed: Feb. 10, 1989

[30] Foreign Application Priority Data

Feb. 10, 1988 [GB] United Kingdom ............... 8802998

[51] Int. Cl.⁵ .......................... G01J 3/26; G01B 9/02
[52] U.S. Cl. ..................................... 356/346; 356/352
[58] Field of Search ................ 356/346, 352; 250/341

[56] References Cited

U.S. PATENT DOCUMENTS 4,730,112  3/1988  Wong .............................. 250/341 X Primary Examiner—Davis L. Willis
Assistant Examiner—Matthew W. Koren
Attorney, Agent, or Firm—Fleit, Jacobson, Cohn, Price, Holman & Stern

[57] ABSTRACT

An optical scanning arrangement for gas sensing, in which scanned light source means produces a spectrum of regularly spaced wavelengths or lines which correspond as regards spacing to the absorption line spectrum of a gas to be monitored and in which the multi-line output from the light source means propagates through a region to be sensed for gas and means for determining the light output from the region for detecting the attenuation of the components of the multi-line output from the light source means due to absorption by said gas being monitored.

6 Claims, 2 Drawing Sheets

OPTICAL SENSING ARRANGEMENTS

This invention relates to optical sensing arrangements and relates more specifically to optical sensing arrangements suitable for optical wavelength scanning to detect the presence or absence of specific wavelengths of light within a certain bandwidth.

In our co-pending patent application Ser. No. 2181536A there is described an optical sensing arrangement for detecting and/or measuring the presence and/or concentration of gas within a specific region to be monitored by scanning a pre-determined relatively narrow bandwidth of broadband (e.g. white) light emerging from or within the region being monitored in order to detect the attenuation of a specific wavelength or spectrum of wavelengths corresponding to an absorption line or line spectrum of the gas being detected. The wavelength scanning is achieved by the use of a Fabry-Perot scanning device having detector means associated therewith. The Fabry-Perot scanning device effectively serves as a so-called "comb" filter which, in response to a sawtooth signal applied to a transducer device of the Fabry-Perot device scans through the periodic (i.e. regularly spaced) absorption wavelength lines of the gas being monitored. This process enables the most efficient use to be made of the light source providing the broadband (e.g. white light) which may comprise a tungsten filament lamp or a light emitting diode. This improved efficiency derived from simultaneously scanning a spectrum of absorption lines of the gas being monitored is complemented by the fact that the gas absorption line spectrum is more effectively recognisable or distinguishable from the line spectrums of other gases by reason of the fact that although the absorption lines of one gas may lie in the same spectral region as those of the other gas, the spacing between the absorption lines of the respective spectrums may be different. Thus greater selectivity is afforded by the scanning of the line spectrum.

The present invention is based upon the realisation that instead of providing a "comb" filter scanning arrangement providing for the simultaneous scanning of the absorption lines of the gas spectrum on the output side of the region being monitored for the detection and/or measurement of concentration of a gas therein, the light source means may be designed and/or arranged to provide a multi-line light output which corresponds or closely approximates to the multi-line spectrum of absorption lines or wavelengths of the particular gas to be monitored as regards the spacing between these lines and the particular spectral band in which they are located.

According to the present invention therefore there is provided an optical scanning arrangement eminently suitable for use as a gas sensor, in which scanned light source means produces a spectrum of regularly spaced wavelengths or lines which correspond as regards spacing to the absorption line spectrum of a gas to be monitored or to some other absorption spectrum or equivalent and in which the mutli-line output from the light source means propagates through a region to be sensed for gas and means for determining the light output from the region for detecting the attenuation of the components of the multi-line output from the light source means due to absorption of said gas being monitored.

According to one mode of carrying out the present invention to provide a "comb" generated source spectrum the light source means may comprise a Fabry-Perot semi-conductor laser or equivalent for producing a variable multi-line output having a line spacing corresponding to the spacing of absorption lines in the absorption line spectrum of the gas to be monitored. The output lines of the laser multi-line output may be scanned simultaneously, as by changing either the laser current bias or laser temperature or by applying mechanical pressure to the laser in order to change the effective optical length of the lasing cavity.

According to another mode of carrying out the present invention to provide a "comb" filtered source spectrum the light source means may comprise a white light source or broadband source such as a light emitting diode or some other luminescent semiconductor device. The light source means will also include a frequency scanning "comb" filter which may be of the Fabry-Perot type or which may comprise a guided Mach-Zehnder interferometer. The material of the laser in the first mode of carrying out the invention will be chosen to give the correct centre frequency at the desired current bias level of the laser for normal operation.

By way of example various embodiments of the present invention will now be described with reference to the accompanying drawings in which.

Figure 4:
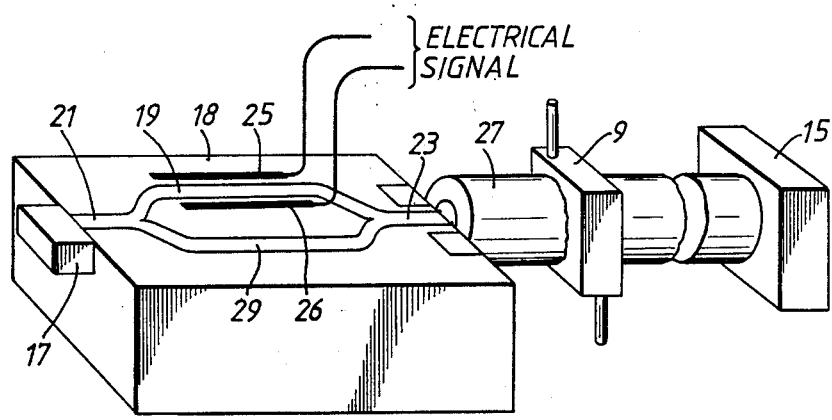
Figure 5:
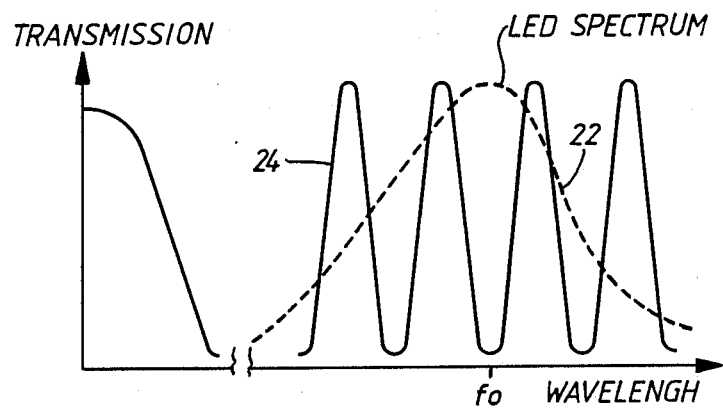

FIG. 4 shows a schematic diagram of another form of optical wavelength spectrum scanning arrangement according to the invention including a Mach-Zehnder interferometer of a form using an integrated optic structure. Alternatively an all-fibre Mach-Zehnder interferometer could be used provided a suitable length-changing means is incorporated in one arm. (This length-changing means could be a piego-electric stretcher; and, FIG. 5 shows the output characteristics of the light source and Mach-Zehnder interferometer of FIG. 4.

Figure 1:
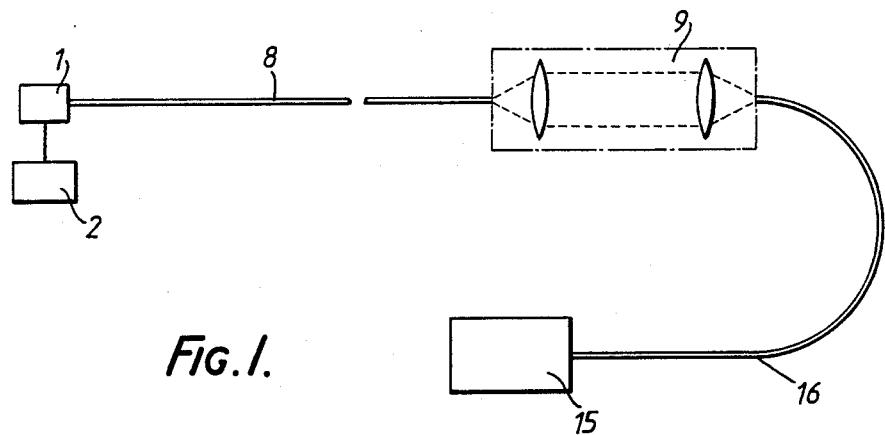
FIG. 1 shows a schematic diagram of one form of optical wavelength spectrum scanning arrangement according to the present invention.
Figure 2:
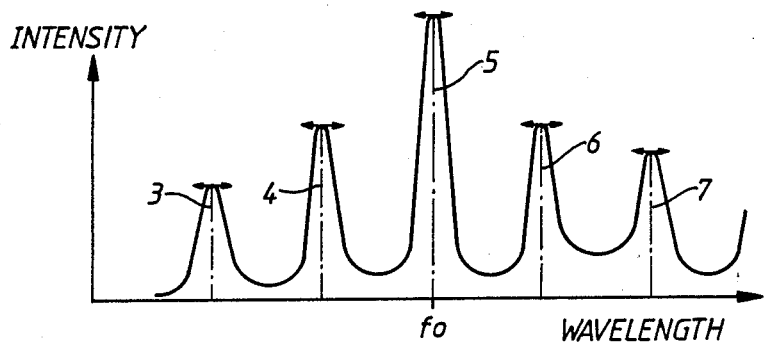
FIG. 2 shows the scanning "comb" or multi-line output from the light source means of the arrangement in FIG. 1.

Referring to FIG. 1 of the drawings the gas sensing arrangement depicted schematically comprises a Fabry-Perot cavity type multi-mode semiconductor laser light source 1 which produces an intensity line spectrum generally of the form shown in FIG. 2 and the material of which is selected in order to produce a centre frequency $f_0$ with the bias input current level of the biasing input means 2 at a desired level.

The spectrum of all of the lines of the laser multi-line output are arranged to be scanned simultaneously as depicted by the double ended arrows associated with the lines 3 to 7 in FIG. 2, conveniently by changing the laser biasing current. Alternatively, the scanning of the lines could be achieved by varying the temperature of the laser or by applying variable mechanical pressure to change the effective optical length of the lasing cavity of the Fabry-Perot laser.

The scanned multi-line output from the laser may be launched into an optical fibre 8 (or free-space or optically collimated path) for transmission to a gas cell 9 located in a region where the presence and/or concentration a of gas (e.g. methane) or gaseous mixture is required to be detected and/or measured.

The gas to be detected will have an absorption line spectrum which causes light at wavelengths corresponding to those absorption lines to be attenuated as the light propagates through the gas cell 9.

For the purpose of detecting a gas in the gas cell 9 the material of the laser 1 is chosen so that the regular spacing between the intensity lines of the multi-line output corresponds to the regular spacing between the absorption lines of the absorption line spectrum of the gas concerned. This regular spacing is specifically individual to and characteristic of a particular gas. Moreover, the wavelength of the absorption lines of the gas will lie within the waveband of the multi-line output from the laser. The absorption line spectrum may typically be of the form shown in FIG. 3 in which absorption lines 10 to 14 are indicated.

As will be appreciated, when the scanned multi-line output propagates through the gas cell 9 the wavelength of the light corresponding to the absorption lines (FIG. 3) will be attenuated according to the presence and/or concentration of the gas within the cell and such attenuation will then be detected by detector means 15 after the light output from the gas cell is transmitted thereto by means of an optical fibre 16 (or free-space or optically collimated paths).

Referring now to FIG. 4 of the drawings, this shows an optical wavelength scanning arrangement in which a broadband light source effectively includes a wavelength scanning "comb" filter. The light source may comprise a light emitting diode 17 or other luminescent semiconductor device. A white light source could alternatively be employed.

The wavelength scanning "comb" filter of the light source means could comprise a Fabry-Perot scanning arrangement of a type similar to that employed at the detector end in the previously referred to co-pending patent application. However, to facilitate the mass production of gas sensing arrangements according to the present invention a guided Mach-Zehnder integrated optics interferometer filter 18 may advantageously be employed as shown in FIG. 4.

This interferometer comprises two monomode branch paths 19 and 20 between which a monomode guided light signal in an input light path 21 is divided. The input guide signal to the interferometer derived from the light emitting diode 17 is depicted in FIG. 5 with the light emitting diode having a spectrum 22 of generally sinusoidal form. The two branched paths 19 and 20 of the interferometer are re-combined into a monomode output guide light path 23. The difference in length of the light paths 19 and 20 is arranged so that the spacing between the cyclic intensity transmission waveform of the interferometer which is generally sinusoidal as can be seen at 24 in FIG. 5 corresponds to the regular spacing between the absorption lines of the absorption spectrum appertaining to the gas to be sensed in the gas cell 9 (see the gas absorption line spectrum of FIG. 3). At the same time the light emitting diode 17 will have a wavelength which is located within the wider absorption line spectrum of the gas to be detected.

Figure 3:
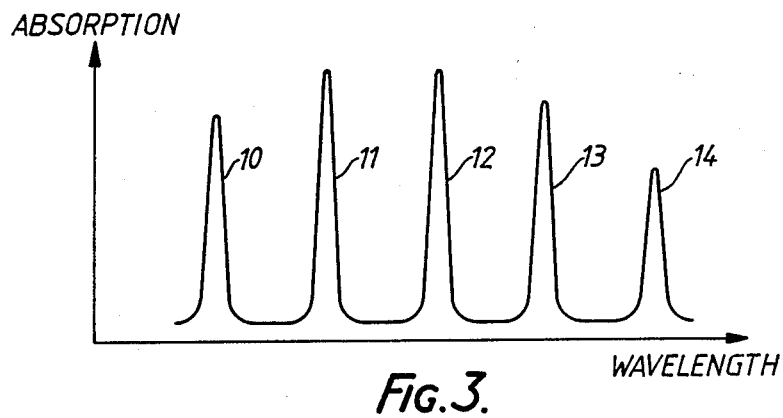
FIG. 3 shows the absorption line spectrum of a gas capable of being monitored by the arrangement of FIG. 1.

The Mach-Zehnder interferometer is provided with a pair of electrodes 25 and 26 situated on the opposite sides of the branch path 19 and by applying variable electrical signals between the electrodes 25 and 26 the length of the optical path 19 may be varied slightly to modulate the output from the light emitting diode which results in frequency or wavelength scanning of the cyclic transmission shown in FIG. 5 whereby the light coupled into an output fibre 27 consists of the desired frequency swept multi-line output with the frequency spacing between transmission intensity peaks or lines being equal or nearly equal to the spacing between the absorption lines of the gas absorption line spectrum (see FIG. 3).

As the in case of the FIG. 1 embodiment, the scanned multi-line output from the light source means will be propagated through the gas cell 9 where the concentration of gas present will cause attenuation of the light intensity lines corresponding to the absorption lines of the gas spectrum and this attenuation will be detected by the detector means 15 for the detection and measurement of gas concentration within the gas cell 9. The Mach-Zehnder interferometer may comprise a lithium niobate substrate intensity modulator with the imbalance between paths being suitably chosen. However, there may be a particular advantage in producing the modulator in semiconductor material so that the light-emitting diode 17 could be embodied in the same monolithic structure as the modulator thereby enabling cost savings to be achieved in mass production of the sensing arrangements.

In yet another embodiment of the present invention the filter may be provided by an integrated surface waveguide modulating arrangement which would be substituted for the Mach-Zehnder interferometer with a $\Delta\beta$ modulator of known form being provided which again effectively acts as a comb filter to scan the multi-line output from the light source.

I claim:

1. An optical scanning arrangement for gas sensing, in which scanned light source means comprising a white or broadband light source and a frequency scanning comb filter produces a spectrum of regularly spaced wavelengths or lines which correspond as regards spacing to an absorption line spectrum or a gas to be monitored and in which a multi-line output from the light source means propagates through a region to be sensed for gas and means for determining the light output from the sensed region for detecting attenuation of components of the multi-line output from the light source means due to absorption by said gas being monitored.

2. An optical scanning arrangement as claimed in claim 1, in which the comb filter is of the Fabry-Perot type.

3. An optical scanning arrangement as claimed in claim 1, in which the comb filter comprises a guided Mach-Zehnder interferometer.

4. An optical scanning arrangement as claimed in claim 3, in which the light source means comprises a semiconductor device and the interferometer comprises two monomode branch paths of different predetermined lengths between which a monomode guided light signal in an input light path is divided, the two branched paths of the interferometer being recombined into a monomode output guide path.

5. An optically scanning arrangement as claimed in claim 4, in which the interferometer comprises a lithium niobate substrate intensity modulator.

6. An optical scanning arrangement as claimed in claim 1, in which the comb filter is provided by an integrated surface waveguide modulating arrangement.

* * * * *